United States Patent [19]
Holmberg et al.

[11] Patent Number: 5,198,493
[45] Date of Patent: Mar. 30, 1993

[54] METHOD OF COVALENTLY BONDING BIOPOLYMER TO A SOLID HYDROPHILIC ORGANIC POLYMER

[75] Inventors: Krister Holmberg, Molndal; Karin Bergstrom, Kungälv, both of Sweden

[73] Assignee: Berol Nobel AB, Stenungsund, Sweden

[21] Appl. No.: 759,018

[22] Filed: Sep. 13, 1991

[30] Foreign Application Priority Data

Sep. 13, 1990 [SE] Sweden .................................. 9002909

[51] Int. Cl.$^5$ ........................ C08H 5/12; C08L 89/00; C08L 1/00
[52] U.S. Cl. ................................. 525/54.1; 525/54.2; 525/54.21; 525/54.23; 525/54.24; 525/54.3; 525/54.31
[58] Field of Search .................. 525/54.1, 54.2, 54.21, 525/54.23, 54.24, 54.28, 54.3, 54.31

[56] References Cited

U.S. PATENT DOCUMENTS 4,898,824  2/1990  Yip ........................................ 435/181

Primary Examiner—Nathan M. Nutter
Assistant Examiner—Jeffrey Culpeper Mullis

[57] ABSTRACT

A process for covalently bonding biopolymer, such as protein, to an organic polymer surface coated with hydrophilic nonionic polymer having groups reactive with the biopolymer, which comprises reacting biopolymer with the surface in a nonpolar reaction medium, preferably a microemulsion, containing from about 0.5 to about 25% water by weight, having a dielectric constant less than 10% of the dielectric constant of pure water; and the product comprises a biopolymer immobilized on a hydrophilic solid surface having a nonionic polymer and a hydrophilic layer, coupled thereto via biopolymer-reactant groups of the nonionic polymer, and accordingly has low spontaneous adsorption of proteins and other biopolymers through electrostatic attraction and/or hydrophobic interaction.

11 Claims, No Drawings

METHOD OF COVALENTLY BONDING BIOPOLYMER TO A SOLID HYDROPHILIC ORGANIC POLYMER

The immobilization of proteins and other biopolymers to solid surfaces is an established technique for a number of biochemical applications, such as solid phase diagnostics, analysis with biosensors, affinity chromatography, extra-corporeal therapy, and bio-organic synthesis. In all of these cases, the biopolymer is bonded to a solid surface, and its biological activity then utilized for a specific purpose, such as in solid phase diagnostics, extracorporeal therapy, biological synthesis, and treatment of implants.

In solid phase diagnostics, an antibody is frequently immobilized on a plastic surface, usually of polystyrene. When in contact with a body fluid, the immobilized antibody bonds any antigen that may be present. The antibody-antigen complex is then detected by means of a labelled antibody. The labelling may be in the form of a radioactive isotope, a fluorescent group, or an enzyme conjugate.

In extracorporeal therapy, a biologically-active substance is bonded to a chamber through which the patient's blood is conducted. A current example of extracorporeal therapy is hemoperfusion across an immobilized immunostimulating substance. Interferons and interleukins are examples of such substances. Examples of diseases that can be treated by this technique are cancer and AIDS.

In bio-organic synthesis, use is made of enzymes for producing organic compounds. An appropriate use for bio-organic synthesis is lipid transformations, i.e. transforming a lipid, usually a triglyceride, into another lipid. Most enzymes are expensive, and frequent reuse is necessary to ensure good process economy. Consequently, the use of immobilized enzymes is of interest in most large-scale enzymatic processes.

In the treatment of implants, a biopolymer is bonded to the surface which comes into contact with biological tissue. The biopolymer, for example collagen, promotes tissue growth and stimulates cell colonization on the implant, resulting in an increased biocompatibility. This technique can be utilized also for in vitro treatment of cell culture dishes to improve cell adhesion.

The immobilization of proteins on both organic and inorganic surfaces is today a well-established technique (see Chapter 4, *Principles of Immobilization of Enzymes, Handbook of Enzyme Biotechnology*, Second Edition, Ellis Horwood Limited, 1985), and it is possible to bond a large amount of protein to the surface while retaining adequate biological activity.

However, it has been found that most solid surfaces are so constituted that they adsorb proteins and other biopolymers spontaneously. Such adsorption from aqueous solution is promoted primarily by two types of physical forces, electrostatic attraction, and hydrophobic interaction. Most surfaces at normal pH are negatively charged, but usually they also contain hydrophobic domains. A protein usually has positive, negative and hydrophobic seats, which means that a protein is attracted to most surfaces, on the one hand by electrostatic attraction between positive seats and negatively charged groups in the surface, and, on the other hand, by hydrophobic interaction between hydrophobic domains of the protein and the surface. This is described in, for example, *Surface and Interfacial Aspects of Biomedical Polymers*, Ed. J. D. Andrade, Plenum Press (1985), Vol. 2, p. 81.

Such nonspecific adsorption by electrostatic attraction and hydrophobic interaction is an undesired phenomenon for the above-mentioned applications. In solid phase diagnostics, it results in an impaired sensitivity and a shorter life of the diagnostic kit. In both extracorporeal therapy and in bio-organic synthesis, spontaneous adsorption causes impaired activity and a shorter product life.

One way of drastically reducing the adsorption of proteins and other biopolymers on solid surfaces is to provide the surfaces with a layer of an uncharged hydrophilic polymer. One example of a polymer that has been used for this purpose is polyethylene glycol (see C. G. Golander, *Preparation and Properties of Functionalized Polymer Surfaces*, Dissertation, Royal Institute of Technology, Stockholm (1986)), but other substances, such as polysaccharides, for example dextran, cellulose ethers and starch; polyvinyl alcohol; and neutral silica sol have also been used for this purpose.

By coating the surface with a layer of uncharged hydrophilic polymer, such as polyethylene glycol side chains or "tails", both electrostatic attraction and hydrophobic interaction can be avoided.

One way of attaching polyethylene glycol tails to a solid polymer surface is first, to subject the surface to so-called acidic etching, then to absorb a cationic polymer, such as polyethylene imine, to the surface, and finally, to react a reactive polyethylene glycol derivative with available amino groups in the polyethylene imine layer. This technique has been described in *Prog. Colloid Polym. Sci.* 74 113–119 (1987). During the acidic etching (which is carried out with potassium permanganate in concentrated sulphuric acid), carboxylic acid and sulphonic acid groups as well as sulphuric acid esters are formed on the surface, forming a highly negatively charged polymer surface, to which the cationic polyethylene imine is bonded very strongly by electrostatic forces. Furthermore, it is likely that upon drying salt bonds between ammomium groups in the polyethylene imine and carboxylate and sulphonate groups on the surface gradually are transformed into amide or imide bonds, which gives an even stronger bond of the polyethylene imine to the surface.

Even though hydrophilized surfaces made by this technique, described in the above paper, give an improved repellency of biopolymers, adsorption by electrostatic attraction and hydrophobic interaction is still much too high for a number of applications.

Hydrophilic surfaces of this type are of great interest in, inter alia, the above-mentioned applications of immobilized proteins. To covalently bond protein to such a surface, it is necessary to introduce into the hydrophilic layer reactive functional groups serving as anchoring points for the protein. However, it has proved extremely difficult to covalently bond protein to thoroughly hydrophilic surfaces, even if the surfaces contain a high concentration of reactive groups. The hydrophilic surface does not attract the protein. On the contrary, it acts as a repellent, because it is energetically unfavorable for a protein in aqueous solution to approach such a surface. As a result, the amount of immobilized protein usually will be low, regardless of whether it is an antibody for solid phase diagnostics, an immuno-stimulating substance for extracorporeal therapy, or an enzyme for bio-organic synthesis. Thus, it is difficult to both adsorb and covalently bond proteins from an aqueous solution to hydrophobic polymer surfaces coated with a thoroughly covering layer of a hydrophilic uncharged polymer, for example polyethylene glycol or a polysaccharide.

In the case of inorganic surfaces, the situation is somewhat different. A recently published work on the immobilisation of lipase on silica shows that considerable amounts of protein can be immobilised on silica treated with polyethylene glycol. Coupling occurs to reactive groups on the free ends of the polyethylene glycol (M. -B. Stark and K. Holmberg: *Biotech. Bioeng.* 34 (1989) 942). This work describes the immobilisation of the protein to the polyethylene glycol-modified surface both from an aqueous solution and from a hexane solution, as well as from a microemulsion containing 94% hexane, 5% tenside and 1% water. A microemulsion is an isotropic and thermodynamically stable solution of a hydrophobic component, water and a surface-active component. The authors show that practically the same amount of lipase is bonded to the polyethylene glycol-coated silica surface in the three experiments conducted with different solvents. Bonding seems to occur independently of the polarity of the solvent.

Surprisingly, it has now been found that biopolymers can be immobilised with good yield on hydrophobic polymer surfaces coated with a layer of a hydrophilic nonionic polymer, such as polyethylene glycol or a polysaccharide, that carries no electrostatic or electric charge, if the immobilisation reaction is carried out in a nonpolar or substantially nonpolar reaction medium. By "biopolymer" primarily protein is meant, but the term also comprises lipids, carbohydrates and lipopolysaccharides. The observation made according to the invention is highly interesting since it implies that the hydrophilic nonionic polymer surface, which by hydrophilisation has been made repellent to proteins from aqueous solution, in this manner can be functionalised with proteins, for example antibodies and antigens. When the reaction is over, the surface is suitably leached in water, causing the hydrophilic polymer layer to be rehydrated, as a result of which the protein is bonded to a highly protein-repellent base.

In accordance with the invention, there is provided a process for covalently bonding biopolymer, such as protein, to an organic polymer surface coated with hydrophilic nonionic polymer having groups reactive with the biopolymer, which comprises reacting biopolymer with the surface in a nonpolar reaction medium, preferably a microemulsion, containing from about 0.5 to about 25% water by weight having a dielectric constant less than 10% of the dielectric constant of pure water; and the product comprises a biopolymer immobilized on a hydrophilic solid surface having a nonionic polymer and a hydrophilic layer, coupled thereto via biopolymer-reactant groups of the nonionic polymer, and accordingly has low spontaneous adsorption of proteins and other biopolymers through electrostatic attraction and/or hydrophobic interaction.

The basic principle of the invention is that the immobilisation reaction is not carried out in water as a reaction medium, the conventional medium for reactions with biopolymers, but in a nonpolar reaction medium which may contain water but has a dielectric constant that is less than 10%, preferably less than 5%, of the dielectric constant of pure water. It has been found use of this reaction medium frequently increases the amount of biopolymer bonded to the surface by more than 10 times.

An especially preferred form of reaction medium is a microemulsion containing an amount of water within the range from about 0.5 to about 25% by weight, preferably from 1 to 15% by weight.

The nonpolar reaction medium or the nonpolar component of a microemulsion is aliphatic hydrocarbon, such as hexane or nonane, or a hydrocarbon distillation fraction, such as 60–80% petroleum ether. The nonpolar component of a microemulsion usually constitutes from about 63 to about 98.5% by weight of a nonpolar microemulsion.

The surface-active component usually is a combination of a surface-active compound or surfactant and a cosurfactant. Anionic, cationic, amphoteric or nonionic surfactants can be used. The combined amount of surfactant and cosurfactant is within the range from about 0.5 to about 20% by weight of microemulsion. The cosurfactant is conventional, and usually is an alcohol or a low-molecular wright alkylene glycol ether. Examples of conventional cosurfactant are butanol, pentanol, hexanol, ethylene glycol monobutyl ether, and diethylene glycol monobutyl ether.

It has been found especially advantageous to use a surfactant capable of forming microemulsions in the absence of a cosurfactant. Surfactants having this ability are nonimic surfactants produced by alkoxylation of long-chain alcohols or alkylphenols with ethylene oxide or combinations of ethylene oxide and propylene and/or butylene oxide, as well as ionic compounds having an ionic hydrophilic group in a non-terminal position on a hydrocarbon chain.

Preferred nonionic tensides have as a hydrophilic group a polyethylene glycol chain which, in the case most preferred, has an average length between three and eight oxyethylene units. The hydrophobic group may derive from hydroxyl compounds or carboxyl compounds containing an alkyl chain having from 8 to 20 carbon atoms, or an alkyl aryl group having from 9 to 24 carbon atoms. Examples of such compounds are ethylene oxide adducts of nonyl phenol, octyl phenol and fatty alcohols.

Preferred ionic tensides have anionic groups such as sulphonate, sulphate, carboxylate, phosphate and phosphonate, sulphonate being especially preferred, attached to a hydrophobic group. Such tensides may also contain alkylene oxide groups, such as ethylene oxide, as coupling agents between the anionic groups and the hydrophobic group. The hydrophobic group may be an alkyl chain having from 10 to 22 carbon atoms, or an alkyl aryl group having from 9 to 24 carbon atoms. A few ether, ester or amide groups may be present in the hydrophobic group. Examples of suitable ionic tensides are di(2-ethylhexyl)sulphosuccinate and carboxymethylated nonyl phenol ethoxylates containing from 1 to 4 ethylene oxide groups.

To covalently bond a hydrophilic nonionic polymer surface to the solid organic polymer, and to covalently bond the biopolymer to the hydrophilic nonionic polymer surface, reactive functional groups are introduced in conventional manner to serve as anchoring points. Examples of reactive groups that can be attached to or occur on the solid organic polymer are amino, carboxyl or hydroxyl groups with which the hydrophilic nonionic polymer or an activated form thereof can react. The hydrophilic polymer preferably comprises reactive groups, such as epoxy, tresylate, carbonyl imidazole and acyl azide groups capable of reacting with reactive groups on the solid polymer and with biopolymer such as protein which is normally bonded via one or more of its amino, thiol and/or phenolic hydroxyl groups. This technique for introduction of reactive functional groups has been described in detail in, inter alia, the above-mentioned references *Surface and Interfacial Aspects of Biomedical Polymers*, Ed. J. D. Andrade, Plenum Press 1985, Vol. 2, p 81, and C. G. Golander: Preparation and Properties of Functionalized Polymer Surfaces, Dissertation, Royal Institute of Technology, Stockholm 1986. In the event that the protein is a glycoprotein, glycolipid or carbohydrate, bonding may occur to aldehyde groups generated in the carbohydrate moiety by oxidation with, for example, sodium periodate. It is also possible to anchor the hydrophilic polymer to the solid polymer in conventional manner by physical adsorption.

The nonionic hydrophilic polymer suitably is polyethylene glycol or randomly distributed or block-distributed polyalkylene glycols between ethylene oxide and alkylene oxide having from 3 to 4 carbon atoms, or tetrahydrofuran. Other groups of suitable polymers are adducts of ethylene oxides, optionally in combination with higher alkylene oxides or tetrahydrofuran, with a dihydroxy or polyhydroxy compound, such as glycerol and pentaerythritol. Polysaccharides, such as dextran and starch; cellulose ethers, such as methyl cellulose, methyl hydroxypropyl cellulose or ethyl hydroxyethyl cellulose; polyvinyl alcohol; and neutral silica sol are other hydrophilic polymers suitable for use with the present invention.

The hydrophilic polymer is water-soluble, and its molecular weight usually is within the range from about 1,000 to about 200,000, preferably from about 2,000 to about 100,000.

The following Examples represent preferred embodiments of the invention.

EXAMPLE 1

Immobilisation of IgG Antibody on Hydrophilic Polystyrene

A 2 cm×2 cm polystyrene plate was made carboxy-functional by plasma polymerisation of acrylic acid on the surface. The carboxyl-functional group was treated with a 10% solution of diaminopropane in water in the presence of water-soluble carbodiimide (0.6%) at pH 4.5–5.0. The plate was rinsed with distilled water and treated with a 10% solution of diepoxidised polyethylene glycol of molecular weight 4,000 at pH 9.5 for 15 hours at room temperature.

To a microemulsion (about 3% of the dielectric constant of water) containing 86% isooctane, 4% sodium bis(2-ethyl hexyl) sulphosuccinate and 10% water (carbonate buffer, pH 9.5) was added 0.05 mg/ml IgG. After mixing, the now hydrophilic plate was treated in this mixture for 4 hours at 40° C. As controls a hydrophilic plate Control (a) as above and another plate Control (b) hydrophilised with polyethylene glycol without epoxide groups were treated in aqueous carbonate buffer of pH 9.5.

The amount of immobilised IgG was measured spectro-photometrically with enzyme-conjugated antibodies against IgG according to the ELISA technique. The amount of adsorbed protein is proportional to the absorbency at 490 mm.

| Sample | OD 495 mm |
|---|---|
| Hydrophilic plate Control (a) with | 0.20 |
| epoxide groups | |
| Hydrophilic plate according to the invention | 2.21 |
| Hydrophilic plate Control (b) without epoxide groups | 0.17 |

EXAMPLE 2

Immobilisation of gamma-Interferon on a Hydrophilised PVC Surface

A 12 cm×8 cm PVC plate intended for an extracorporeal chamber was grafted with crotonic acid under irradiation with UV light of wavelength 320 nm and in the presence of benzophenone as initiator. The resulting carboxyl-functional surface was treated with a 10% aqueous solution of polyethylene imine in the presence of water-soluble carbodiimide (0.6%) at pH 4.5–5.0. The plate was then treated with a 10% solution of polyethylene glycol 4000 dicarbonyl imidazole at pH 8.0 for 3 hours at room temperature. To a microemulsion (about 3% of the dielectric constant of water) containing 82% isooctane, 8% pentaethylene glycol mono(n-dodecyl ether) and 10% water (borate buffer, pH 8.0) was added 50,000 units gamma-Interferon. The plate was treated with this microemulsion for 2 hours at 40° C.

Peripheral mononuclear blood cells were isolated by gradient centrifugation on Lymphoprep. The cells were diluted to $1.10^6$/ml in RPMI 1640, 10% FCS, 1% PEST and incubated on the gamma-Interferon-immobilised plate for 7 days at 37° C. and 5% $CO_2$.

As a control, the above was repeated using a plate which after hydrophilisation was treated with gamma-Interferon in aqueous borate buffer of pH 8.

Neopterin was used as a marker for cell stimulation. It is well known that lymphocytes and macrophages secrete neopterin when stimulated by, inter alia, gamma-Interferon.

| | Neopterin (nmol/l) |
|---|---|
| Immobilisation according to the invention | 67 |
| Control | 5 |

EXAMPLES 3 TO 5

Comparison between adsorption and immobilisation on a hydrophilic inorganic material (glass) and on a hydrophobic organic polymer (polystyrene)

A 2 cm×6 cm glass plate was washed first with ethanol, then with 1M HCl, and finally with 30% hydrogen peroxide. The plate was then reflux-boiled for 16 hours in 150 ml of a 10% solution of 3-amino propyl trimethoxy silane in toluene. To the glass amino-functionalised in this manner was added a solution of 10 g diepoxidised polyethylene glycol (molecular weight 1,500) in 40 g 0.1M carbonate buffer of pH 9.0. After 24 hours at 37° C., the glass plate was removed from the solution. ESCA analysis shows that a dense polyethylene glycol layer had been formed on the surface. Then a solution of 0.05 mg/ml IgG antibody in 0.1M carbonate buffer, pH 9.0, was added to the plate. The immobilisation reaction was finished after 24 hours at 37° C. A corresponding immobilisation of IgG onto the modified glass surface was made also from a microemulsion, use being made of the same microemulsion composition and the same reaction conditions as in Example 1.

A polystyrene plate having the same dimensions as the glass plate was activated with a solution of $KMnO_4$ in concentrated $H_2SO_4$ for 30 seconds at 20° C. The plate was then made amino-functional by adsorption of polyethylene imine, whereupon treatment with polyethylene glycol derivative and immobilisation of IgG antibodies, both from water and from microemulsion, was carried out in the same way as described above for the glass plate.

The amount of immobilised IgG antibody was determined spectrophotometrically with enzyme-conjugated antibodies against IgG according to the ELISA technique. Nonspecific adsorption of the antibodies was also determined on polyethylene glycol-modified plates which had not been subjected to protein coupling, but instead had been made nonreactive by treatment with 1M $HClO_4$ for 1 hour at 20° C., the epoxide rings at the ends of the polyethylene glycol chains being opened.

The amount of covalently bonded and adsorbed IgG on the modified glass and polystyrene plates is shown in Table I below. The amount of adsorbed proteins is proportional to the adsorbency at 490 nm.

TABLE I

| Example | | OD 495 nm |
|---|---|---|
| Control 1 | Hydrophilic glass plate, covalent bonding from water | 2.30 |
| Control 2 | Hydrophilic glass plate, covalent bonding from microemulsion | 2.15 |
| Control 3 | Hydrophilic glass plate, adsorption from water | 2.05 |
| Control 4 | Hydrophilic polystyrene plate, covalent bonding from water | 0.25 |
| Control 5 | Hydrophilic polystyrene plate, covalent binding from microemulsion | 1.90 |
| Control 6 | Hydrophilic polystyrene plate, adsorption from water | 0.15 |

The results indicate that good immobilisation of proteins is obtained on an organic polymer, such as polystyrene, when immobilisation is carried out in a reaction medium according to the invention. If the surface is a hydrophilic inorganic material, such as glass, the effect of the reaction medium on the immobilisation is marginal, and at the same time a high undesirable adsorption is obtained.

Having regard to the foregoing disclosure, the following is claimed as the inventive and patentable embodiments thereof:

1. A process for covalently bonding biopolymer to an organic polymer surface coated with a hydrophilic nonionic organic polymer surface having groups reactive with the biopolymer which comprises reacting biopolymer with the reactive groups of the nonionic hydrophilic polymer in a nonpolar reaction medium having a dielectric constant less than 10% of the dielectric constant of water.

2. A process according to claim 1, in which the reaction is carried out in a reaction medium having a dielectric constant less than 5% of the dielectric constant of water.

3. A process according to claim 1, in which the reaction medium comprises aliphatic hydrocarbon.

4. A process according to claim 1, in which the reaction is carried out in a microemulsion containing water in an amount from about 0.5 to about 25% by weight.

5. A process according to claim 4, in which the amount of water is from about 1 to about 15% by weight.

6. A process according to claim 4, in which the biopolymer is a protein and is bonded via at least one of amino, thiol and phenolic hydroxyl groups, to an epoxy, tresylate, carbonyl imidazole or acyl azide group in the hydrophilic nonionic polymer.

7. A process according to claim 1 in which the biopolymer is a protein which is bonded to hydrophilic nonionic polymer that is a polyethylene glycol having reactive groups.

8. A process according to claim 1, in which the reaction medium is a microemulsion comprising as a surfactant a nonionic polyalkylene oxide derivative having from three to eight oxyethylene units.

9. A process according to claim 1, in which the reaction medium is a microemulsion comprising as a surfactant a hydrocarbon sulphonate.

10. A process according to claim 1, in which the reaction medium is a microemulsion containing from 0.5 to 20% by weight of surfactant which is a hydrocarbon sulphonate 63-98.5% by weight of aliphatic hydrocarbon.

11. A process according to claim 1, in which the reaction medium is a microemulsion containing from 0.5 to 20% by weight of surfactant which is a nonionic compound having as a hydrophilic group a polyalkylene oxide having an average of from three to eight oxyethylene units.

* * * * *